US00PP19609P2

(12) United States Plant Patent
Emmett

(10) Patent No.: US PP19,609 P2
(45) Date of Patent: Dec. 30, 2008

(54) ***PRUNELLA* PLANT NAMED 'SUMMER DAZE'**

(50) Latin Name: *Prunella×grandiflora*
Varietal Denomination: Summer Daze

(76) Inventor: Martin Emmett, Binsted Nursery, Binsted La., Binsted, Arundel, West Sussex (GB), BN18 0LL ( * ) Notice: Subject to any disclaimer, the term of this patent is extended or adjusted under 35 U.S.C. 154(b) by 0 days.

(21) Appl. No.: 11/890,079

(22) Filed: Aug. 3, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Kent L Bell

(57) ABSTRACT

A new and distinct cultivar of *Prunella* named 'SUMMER DAZE' that is characterized by dense matting habit, long flowering season, long flower heads, clear pink-purple flowers, and medium green leaves. In combination these traits set 'SUMMER DAZE' apart from all other existing varieties of *Prunella* known to the inventor.

2 Drawing Sheets

Genus: *Prunella.*
Species: *laciniata×grandiflora.*
Denomination: 'SUMMER DAZE'.

BACKGROUND OF THE INVENTION

The present invention relates to a new and distinct cultivar of self-heal that is grown for use as an ornamental garden plant. The new cultivar is known botanically as *Prunella laciniata×grandiflora* and will be referred to hereinafter by the cultivar name 'SUMMER DAZE'.

In 1999 the inventor began a breeding program with the objective of developing new garden cultivars of *Prunella* species. The program was carried out at a nursery in West Sussex, United Kingdom. The inventor commenced the breeding program by placing a single plant of *Prunella laciniata* (species, unpatented) as the intended female parent, within a population of plants of *Prunella grandiflora* (species, unpatented) as potential male parent. The flowers of the *Prunelia laciniata* plant were found to be fertilized and the inventor was able to collect enough seed to yield 48 first generation seedlings. The inventor observed the growth and flowering of these seedlings for two years, and selected 30 plants with promising characteristics of bright flower color and sturdy plant habit. The inventor set aside these plants in a block and allowed them to be open pollinated. Enough seed was collected to raise 100 plants which were then grown for a further two years in order to identify if any of the plants was worthy of commercial introduction.

In 2004, the inventor selected a single plant, 'SUMMER DAZE', for its unique combination of attractive and commercially valuable characteristics including sturdy plant habit, medium-green colored foliage, and long flower heads with clear pink-purple flowers which are borne over a long flowering season.

'SUMMER DAZE' differs from the male parent by exhibiting a longer flowering season and increased vigor. 'SUMMER DAZE' differs from the female parent by exhibiting leaves which are barely or occasionally lobed, whereas the foliage of the female parent consists of deeply cut lobes. The closest comparison plant known to the inventor is *Prunella* 'Bella Deep Rose' (unpatented). In comparison with 'Bella Deep Rose', the flowers of 'SUMMER DAZE' are clear pink-purple in color, are borne in longer and larger heads, have a longer flowering season and retain an attractive purple coloration as the flowers age. The flowering duration of *Prunella* 'Bella Deep Rose' is 4 weeks, and its flowers becoming unsightly with age, whereas the flowering duration of 'SUMMER DAZE' is in excess of 8 weeks and the flowers remain attractive by developing a purple coloration with age.

'SUMMER DAZE' is suitable for planting in garden borders or in containers as single subjects or mixed with other plants. Cultural conditions include full sun to filtered shade, moderate water, and organic loamy soil or substrate. 'SUMMER DAZE' reaches 25 cm. in height and 25 cm. in width during the first year, and is hardy to USDA Zone 5.

The first asexual propagation of 'SUMMER DAZE' was conducted by the inventor in Binsted Arundel, United Kingdom in 2005 using basal cuttings. The inventor has determined that the distinguishing characteristics of 'SUMMER DAZE' have remained stable and uniform, and to be reproduced true to type in subsequent generations of asexual propagation.

SUMMARY OF THE INVENTION

The following traits have been repeatedly observed and represent the distinguishing characteristics of the new Prunella cultivar named 'SUMMER DAZE'. These traits in combination distinguish 'SUMMER DAZE' from all other varieties of *Prunella* known to the inventor. 'SUMMER DAZE' has not been tested under all possible conditions. Phenotypic differences might occur with variations in environmental, climatic, and cultural conditions without however, any variance in genotype.

1. 'SUMMER DAZE' exhibits sturdy and dense plant habit.
2. 'SUMMER DAZE' exhibits clear pink-purple flowers and long flower heads.
3. 'SUMMER DAZE' exhibits a long flowering season.
4. The flowers of 'SUMMER DAZE' turn purple with age.
5. 'SUMMER DAZE' exhibits medium-green leaves.

6. 'SUMMER DAZE' is suitable for use as a garden plant and as a component in planted containers.
7. 'SUMMER DAZE' reaches 25 cm. in height and 25 cm. in width during the first year.
8. 'SUMMER DAZE' is hardy to USDA Zone 5.
9. 'SUMMER DAZE' is asexually propagated by methods of division and cuttings.

BRIEF DESCRIPTION OF THE DRAWINGS

The accompanying color drawings illustrate the overall appearance of the new *Prunella* cultivar named 'SUMMER DAZE' showing color as true as it is reasonably possible to obtain in color reproductions of this type. Color in the drawings may differ from color values cited in the detailed botanical description, which accurately describe the actual color of the new variety 'SUMMER DAZE'. The plants depicted in the drawings are 12-months-old and were grown in a retractable roof greenhouse without heat.

The drawing labeled

The drawing labeled

Figure 1:
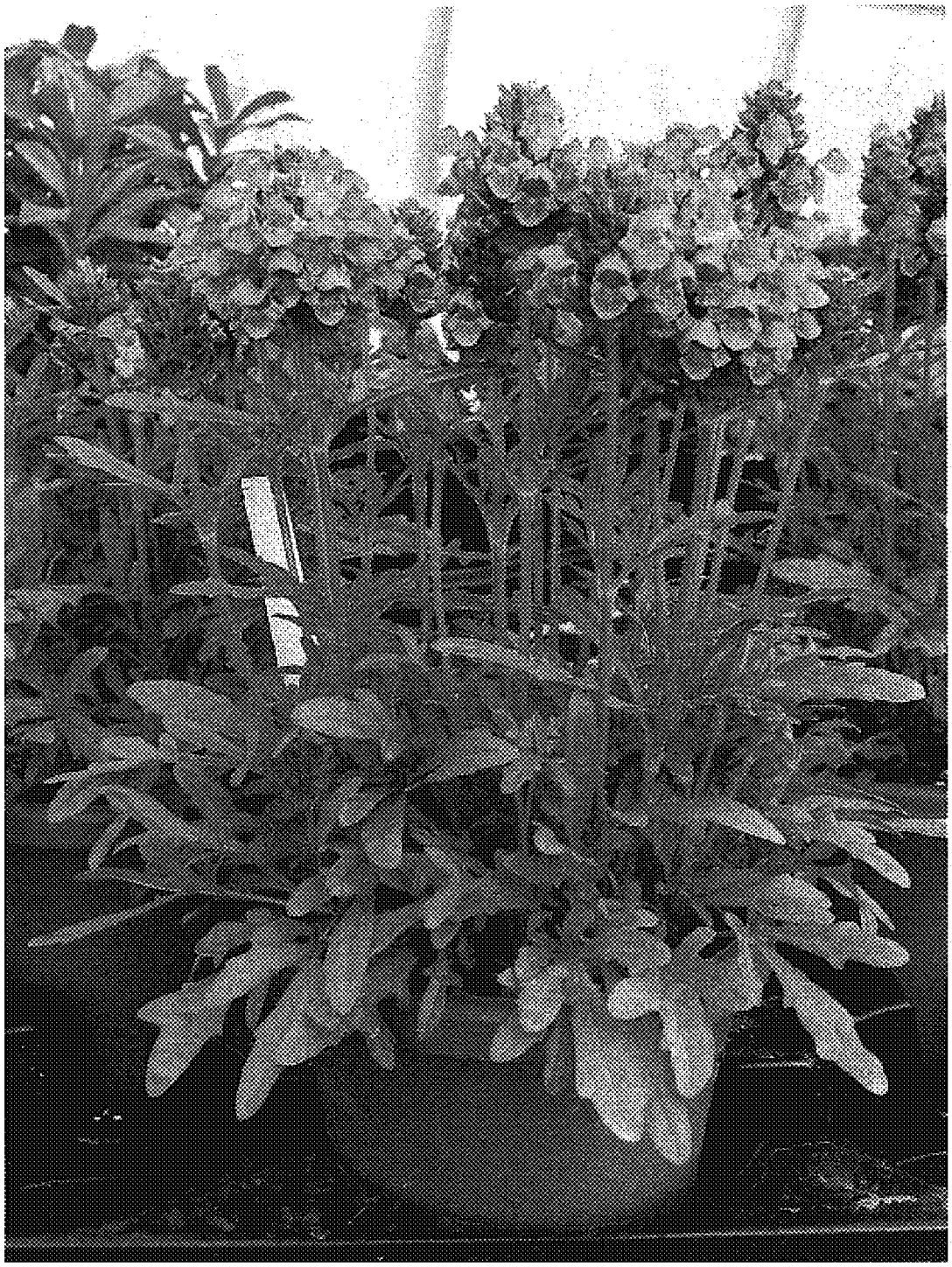
FIG. 1 depicts a whole plant in bloom from a side perspective.
Figure 2:
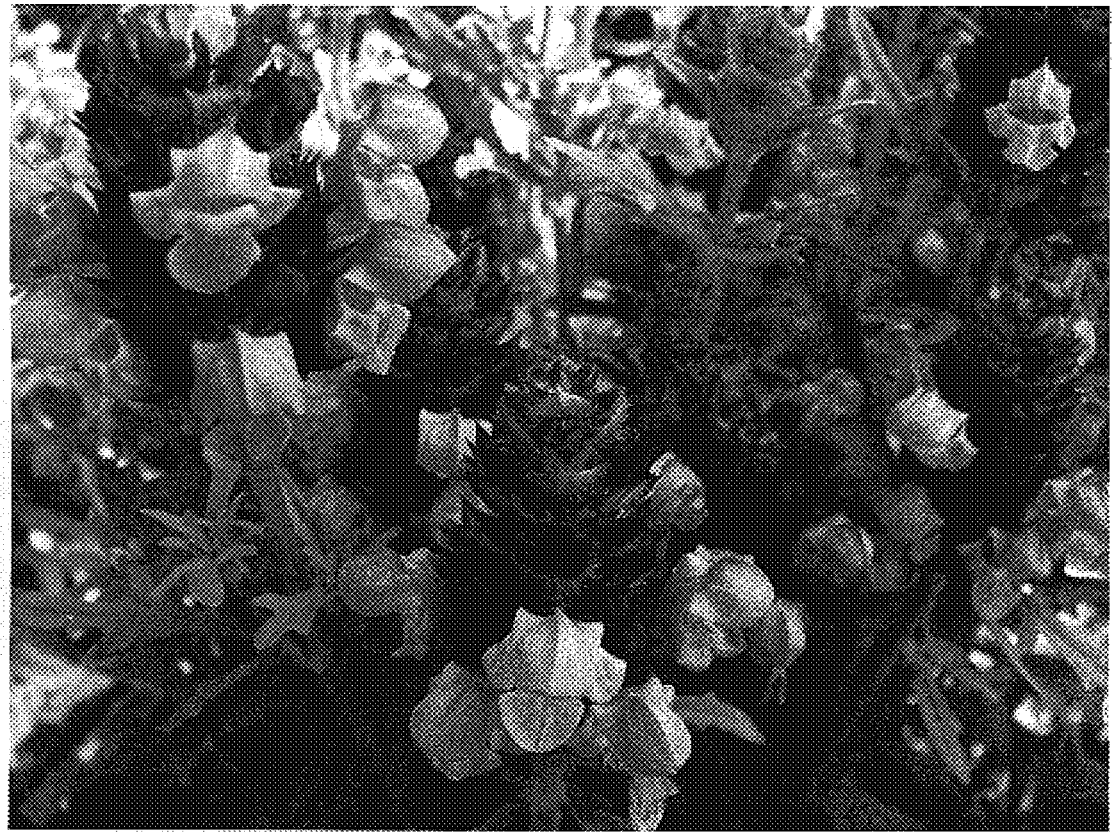
FIG. 2 depicts a close-up view of the flower heads.

Both drawings were made using conventional techniques and although flower and foliage color may differ from actual color due to light reflectance, they are as accurate as can be portrayed by conventional photography.

BOTANICAL DESCRIPTION OF THE PLANT

The following is a detailed botanical description of the new *Prunella* cultivar named 'SUMMER DAZE'. Observations, measurements, values and comparisons were collected over a two month period in Arroyo Grande, Calif. from one year old plants grown out of doors in 14 cm. containers. Color determinations were made in accordance with The Royal Horticultural Society Colour Chart of 2001 except where general color terms of ordinary dictionary significance are used. The growing requirements of the new variety are similar to the species.

Botanical classification: *Prunella laciniata×grandiflora* 'SUMMER DAZE'.
Family: Lamiaceae.
Genus: *Prunella.*
Species: *laciniata×grandiflora.*
Denomination: 'SUMMER DAZE'.
Common name: Self-heal.
Parentage:
*Female parent.*—*Prunella laciniata.*
*Male parent.*—*Prunella grandiflora.*
Asexual propagation methods: Division and cuttings.
Rooting: Tough and deeply rooted.
Time to develop roots (range): 6–8 weeks to develop roots from an initial cutting.
Crop time (range): 9–12 months to produce a finished 2-liter container from a rooted cutting.
Habit: Dense matting habit.
Commercial classification: Ornamental perennial and container plant.
Use: Garden beds, planted containers.
Vigor: Vigorous.
Plant dimensions (first year): 25 cm. in height and 25 cm. in width.
Hardiness: USDA Zone 5.
Cultural requirements: Full sun to filtered shade, moderate water, and organic loamy soil or substrates.
Pest and disease resistance or susceptibility: None of note.
Foliage:
*Type.*—Semi-evergreen.
*Arrangement.*—Opposite.
*Division.*—Simple.
*Shape.*—Lyrate.
*Margin.*—Pinnatilobate.
*Length* (*range*).—3.50 cm–5.25 cm.
*Width* (*range*).—3 cm–4 cm.
*Apex.*—Rounded.
*Base.*—Truncate.
*Venation pattern.*—Pinnate.
*Vein color* (*adaxial surface*).—137B.
*Vein color* (*abaxial surface*).—146A.
*Leaf surface* (*adaxial*).—Puberulent
*Leaf surface* (*abaxial*).—Puberulent.
*Leaf color* (*adaxial surface*).—137B.
*Leaf color* (*abaxial surface*).—146A.
*Leaf attachment.*—Petiolate.
*Petiole shape.*—Sulcate.
*Petiole surface.*—Villous.
*Petiole color.*—144B.
*Petiole dimensions.*—3 cm. in length and 2 mm. in diameter.
*Leaf fragrance.*—None observed.
Flower:
*Inflorescence.*—Verticillaster.
*Inflorescence shape.*—Deltoid.
*Inflorescence dimensions* (*average*).—4 cm. in length and 2.25 cm. in width.
*Flower quantity* (*average*).—20 per inflorescence.
*Flower shape.*—Galeate.
*Flower dimensions.*—2 cm. in length and 1.25 cm. in depth.
*Corolla tube dimensions.*—1 cm. in length and 0.40 cm. in diameter.
*Flower color.*—73A, aging to N74B.
*Corolla tube color.*—155B.
*Upper lip shape.*—Hooded.
*Lower lip shape.*—Tri-lobed and deflexed.
*Upper lip apex.*—Obtuse.
*Lobe apex* (*lower lip*).—Rounded.
*Upper lip margin.*—Entire.
*Lobe margins* (*lower lip*).—Combination of entire and serrated.
*Upper lip color* (*adaxial and abaxial surfaces*).—73A.
*Lower lip color* (*adaxial and abaxial surfaces*).—73A.
*Lips fused or unfused.*—Fused.
*Upper lip surface* (*adaxial and abaxial*).—Glabrous.
*Lower lip surface* (*adaxial and abaxial*).—Glabrous.
*Bud shape.*—Ovate.
*Bud surface.*—Puberulent.
*Bud color.*—N79C.
*Bud height.*—0.60 cm.
*Bud width.*—0.50 cm.
*Bud apex.*—Obtuse.
*Calyx shape.*—Tubular.
*Calyx surface.*—Villous.
*Calyx color.*—Initially green, N138B, becoming 187A at flowering and after flowers drop.
*Calyx height.*—1 cm.
*Calyx width.*—0.60 cm.
*Number of sepals.*—5 in number.
*Sepals fused or unfused.*—Fused.

*Sepal surface* (*adaxial*).—Villous.
*Sepal surface* (*abaxial*).—Villous.
*Sepal color* (*adaxial and abaxial surfaces*).—Initially green, N138B, becoming 187A.
*Sepal apex.*—Acute.
*Peduncle shape.*—Quadrilateral.
*Peduncle surface.*—Lanate.
*Peduncle color.*—Initially green, N138B, becoming 187A.
*Peduncle length.*—5 cm.
*Peduncle width.*—2.75 cm.
*Bract* (*per inflorescence*).—2 at base of peduncle.
*Bract shape.*—Hastate.
*Bract surface* (*adaxial and abaxial*).—Villous.
*Bract color* (*adaxial and abaxial surfaces*).—N138B.
*Bract dimensions* (*average*).—3.25 cm. in length and 1.50 cm. in width.
*Bract apex.*—Acute.
*Bract base.*—Attenuate.
*Bract margin.*—Entire.
*Facing aspect.*—Facing outward and upward.
*Flowering season.*—Summer months.
*Flower fragrance.*—Slight sweet scent.

Reproductive organs:
*Stamens.*—4 in number:
*Stamen length* (*range*).—1 cm–2 cm.
*Stamen color.*—155A.
*Anther color.*—155A.
*Pollen color.*—163A.
*Pollen quantity.*—Small amount.
*Pistil.*—1 in number.
*Pistil shape.*—Filiform.
*Pistil length.*—2.25 cm.
*Pistil color.*—155A.
*Stigma shape.*—Bifid.
*Stigma width.*—2 mm.
*Stigma color.*—155A.
*Ovary position.*—Inferior.
*Ovary shape.*—Ovate.
*Ovary height.*—2 mm.
*Ovary width.*—1 mm.
*Ovary color.*—139A.
Seed: No seed has been observed.

What is claimed is:

1. A new and distinct variety of *Prunella* plant named 'SUMMER DAZE' as illustrated and described herein.

* * * * *